United States Patent
Tipler et al.

(10) Patent No.: US 7,267,709 B2
(45) Date of Patent: *Sep. 11, 2007

(54) METHODS AND SYSTEMS FOR CHARACTERIZING A SORBENT TUBE

(75) Inventors: Andrew Tipler, Trumbull, CT (US); Neil T. Plant, Sheffield (GB)

(73) Assignee: PerkinElmer LAS, Inc., Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/559,760

(22) Filed: Nov. 14, 2006

(65) Prior Publication Data

US 2007/0068385 A1 Mar. 29, 2007

Related U.S. Application Data

(62) Division of application No. 11/072,371, filed on Mar. 4, 2005, now Pat. No. 7,168,296.

(51) Int. Cl.
*B01D 53/02* (2006.01)

(52) U.S. Cl. .............. 95/82; 95/87; 96/102; 73/23.35

(58) Field of Classification Search .............. 95/22, 95/82–89; 96/101–107; 73/23.35–23.42; 422/89

See application file for complete search history.

(56) References Cited

U.S. PATENT DOCUMENTS

| | | | | |
|---|---|---|---|---|
| 4,849,179 A | * | 7/1989 | Reinhardt et al. | 422/89 |
| 4,871,453 A | * | 10/1989 | Kumar | 210/198.2 |
| 5,379,629 A | * | 1/1995 | Muller | 73/23.27 |
| 5,467,635 A | * | 11/1995 | Nakagawa et al. | 73/23.35 |
| 5,545,252 A | * | 8/1996 | Hinshaw et al. | 95/15 |
| 5,792,423 A | | 8/1998 | Markelov | 422/83 |
| 5,932,482 A | | 8/1999 | Markelov | 436/181 |

(Continued)

FOREIGN PATENT DOCUMENTS

EP 0 730 151 A2 9/1996

OTHER PUBLICATIONS

The Diffusive Monitor, Health and Safety Executive Committee on Analytical Requirements, Dec. 2003, Issue 14, 18 pages.

(Continued)

*Primary Examiner*—Duane Smith
*Assistant Examiner*—Robert Clemente
(74) *Attorney, Agent, or Firm*—St. Onge Steward Johnston & Reens LLC

(57) ABSTRACT

Disclosed are systems and methods that include providing a vessel having an adsorbent disposed therein, the vessel having an inlet and an outlet for communicating a carrier gas through the vessel; determining a differential pressure between the inlet and the outlet for a known flow rate at the outlet; and, determining a geometric measure for the vessel based on a ratio of the known flow rate and the differential pressure. In some embodiments, the methods and systems can include a viscosity in the ratio, determining a flow rate at ambient pressure using a factor based on a ratio of a gas pressure at the output and ambient pressure, and/or, determining a flow rate at ambient temperature using a factor based on a ratio of a temperature at the output and ambient temperature.

13 Claims, 8 Drawing Sheets

U.S. PATENT DOCUMENTS

| | | | |
|---|---|---|---|
| 6,338,823 B1 * | 1/2002 | Furukawa | 422/89 |
| 6,341,520 B1 * | 1/2002 | Satoh et al. | 73/23.35 |
| 6,395,560 B1 | 5/2002 | Markelov | 436/181 |
| 6,649,129 B1 * | 11/2003 | Neal | 422/89 |
| 6,652,625 B1 | 11/2003 | Tipler et al. | 95/82 |
| 7,111,494 B2 * | 9/2006 | Tipler | 73/23.36 |
| 2003/0015019 A1 | 1/2003 | O'Brien | 73/23.2 |
| 2004/0129057 A1 | 7/2004 | Bonne et al. | 73/25.03 |
| 2005/0063865 A1 | 3/2005 | Bonne et al. | 422/68.1 |

OTHER PUBLICATIONS

Li Chenghong et al: Optimal Packing Characteristics of Rolled, Continuous Stationary-Phase Columns, Biotechnology Progress, vol. 18, No. 2, Mar. 2002, pp. 309-316, CP002334402. issn: 8756-7938—p. 311, left-hand column, paragraph 2, p. 314, right-hand column, last paragraph; Table 5—(4 Pages).

* cited by examiner

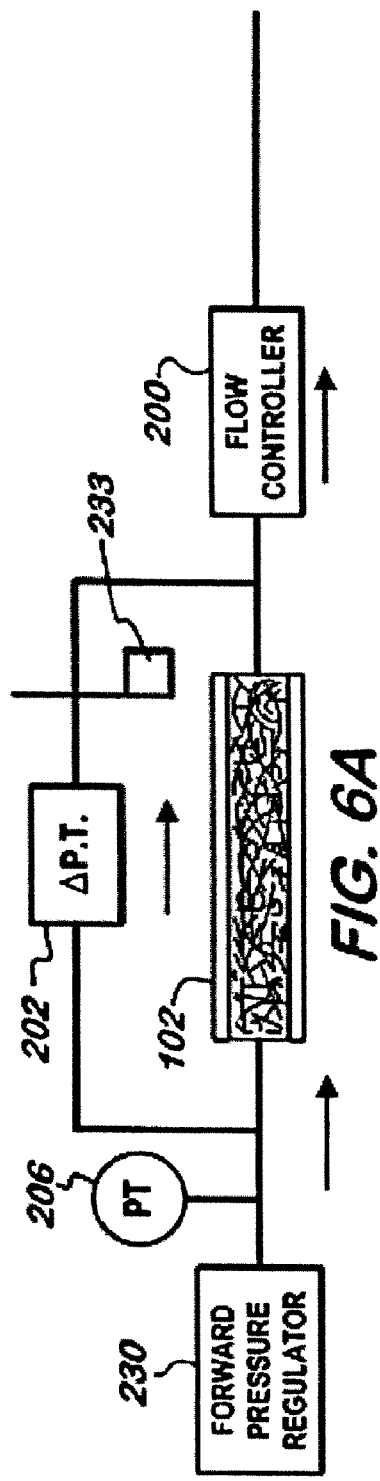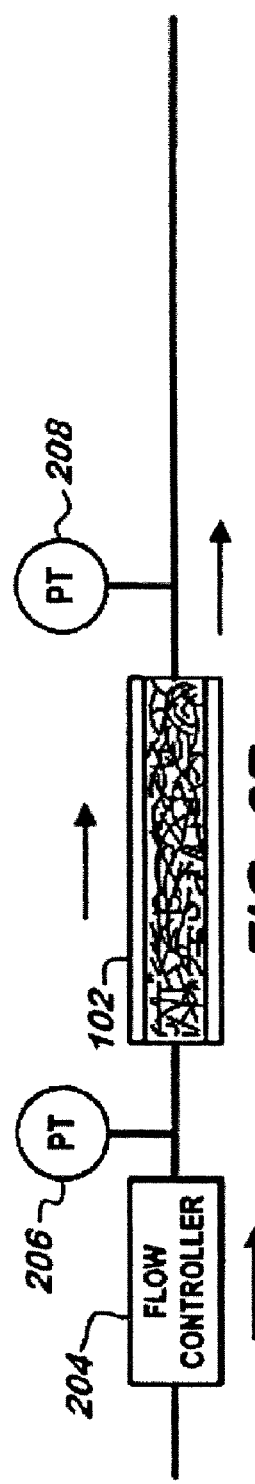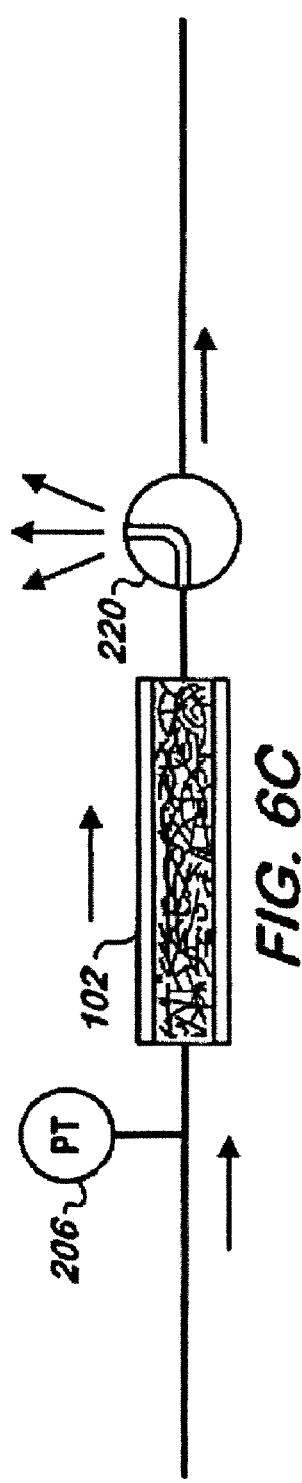

METHODS AND SYSTEMS FOR CHARACTERIZING A SORBENT TUBE

PRIOR APPLICATION

This application is a divisional of U.S. patent application Ser. No. 11/072,371, filed Mar. 4, 2005, now U.S. Pat. No. 7,168,296.

FIELD OF THE INVENTION

The present invention relates to systems and methods for measuring the integrity of a sorbent tube that can be used, for example, in chromatographic systems. More specifically, the invention relates to methods and systems that include a measurement of a geometric characteristic of the sorbent tube.

BACKGROUND OF THE INVENTION

Sorbent tubes have many different applications, and include a packing material that can be used for adsorption. One application for sorbent tubes includes gas chromatography. Gas chromatography is essentially a physical method of separation in which constituents of a test sample in a carrier gas are adsorbed or absorbed and then desorbed by a stationary phase material in a column. A pulse of the sample is introduced into a steady flow of carrier gas, which carries the sample into a chromatographic column. The inside of the column is lined with a liquid, and interactions between this liquid and the various components of the sample—which differ based upon differences among partition coefficients of the elements—cause the sample to be separated into the respective elements. At the end of the column, the individual components are more or less separated in time. Detection of the gas provides a time-scaled pattern, typically called a chromatogram, that, by calibration or comparison with known samples, indicates the constituents, and the specific concentrations thereof, which are present in the test sample. An example of the process by which this occurs is described in U.S. Pat. No. 5,545,252 to Hinshaw.

One common application of chromatographic analysis is the use of thermal desorption units to determine the constituents of a particular environment. For example, it is often desired to detect the amount of volatile organic compounds (VOCs) present in a certain sample of air. One way of doing this is by first transporting a tube packed with an adsorbent material into the environment to be tested, and allowing the VOCs in the air to migrate into the tube through natural diffusion, typically termed "diffusive" or "passive sampling." Alternatively, the VOCs may be collected by drawing a sample of gas (typically ambient air) through such a tube using a small vacuum pump, commonly referred to as "pumped sampling." In each case, the analytes to be measured (i.e., the VOCs) are retained by and concentrated on the adsorbent as the air passes through the tube. As is briefly described in U.S. Pat. No. 6,649,129 to Neal, once the VOCs are first collected in this fashion, and then, the tube is subsequently heated in a thermal desorption instrument, and a flow of inert gas, such as Helium or Nitrogen, is applied to the tube to sweep the VOCs out of the tube and into the chromatographic column for separation and analysis.

Regardless of what particular application is being used, it is also often desired to pre-concentrate the analytes in the sample, and occasionally, remove moisture therefrom, prior to introducing the sample into the chromatographic column. Accordingly, as disclosed in U.S. Pat. Nos. 5,792,423 and 6,395,560 to Markelov, these systems will typically include some kind of "trap" for this purpose, which retains the analytes as they are carried through the trap, and which are later released from the trap, usually by heating, and swept into the chromatographic column. One example is an adsorbent trap, which typically includes a tube packed with a suitable adsorbent material, which adsorbs the analytes as the sample gas first passes through the tube, and from which the analytes are subsequently desorbed into the chromatographic column, such as the arrangements disclosed in U.S. Pat. No. 5,932,482 to Markelov and U.S. Pat. No. 6,652,625 to Tipler. flow rate at a tube outlet. Although the illustrated embodiments include applications directed to gas chromatography systems and methods, it can be understood that the present teachings can be equally applied to other sorbent tube applications.

In an embodiment, the present teachings include methods that include providing a vessel having an adsorbent disposed therein, the vessel having an inlet and an outlet for communicating a carrier gas through the vessel, determining a differential pressure between the inlet and the outlet for a known flow rate at the outlet; and, determining a geometric measure for the vessel based on a ratio of the known flow rate and the differential pressure. In determining a differential pressure, the methods can include providing at least one sensor to provide measurements related to the differential pressure. Determining a geometric measure can also include factoring a viscosity of the carrier gas in the ratio. In embodiments, the vessel may include an adsorbent trap or a sample tube. The methods can further include one or more of determining a flow rate at ambient pressure using a factor based on a ratio of a gas pressure at the output and ambient pressure, and, determining a flow rate at ambient temperature using a factor based on a ratio of a temperature at the output and ambient temperature.

In some embodiments, the present teachings relate to a chromatographic method that includes providing a vessel in a carrier gas flow path to a chromatographic column, where the vessel includes a gas inlet, a gas outlet, and, an adsorbent disposed in the vessel. The chromatographic methods also include measuring a differential pressure along the length of the adsorbent, determining a flow rate at the outlet, and, determining a unit flow per unit pressure based on a ratio of the flow rate and the differential pressure. In some embodiments, the methods can include adjusting the unit flow per unit pressure based on a viscosity of the gas. In embodiments, the chromatographic methods include determining (i) a flow rate at ambient pressure using a factor based on a ratio of a gas pressure at the output and ambient pressure, and/or, (ii) a flow rate at ambient temperature using a factor based on a ratio of a temperature at the output and ambient temperature.

In an embodiment, the present teachings thus comprise a chromatographic system, including a carrier gas inlet for supplying carrier gas, a chromatographic column for receiving the carrier gas, a flow path through which the carrier gas is communicated from the carrier gas inlet to the chromatographic column, a vessel disposed in the flow path, the vessel having an adsorbent disposed therein, wherein the vessel includes an inlet and an outlet for communicating the carrier gas through the vessel, and, at least one sensor in communication with said flow path, the at least one sensor providing at least one However, one problem that exists in these various systems is that the sorbent tubes serving as the traps, as well as the sorbent tube serving as initial sampling tubes when dealing with applications involving the traditional thermal desorption units discussed above, is that the integrity of these tubes is sometimes compromised. Several causes of this problem are illustrated in FIGS. 1A-B. For example, in order for thermal desorption to work successfully, the adsorbent 10 must be properly packed inside the tube 12. However, sometimes this does not occur, and voids 14 are formed in the adsorbent, as shown in FIG. 1A. These voids will channel some of the gas flow, thereby degrading the adsorption and desorption efficiency of the adsorbent packing.

Similarly, occasionally, the adsorbent becomes damaged as a result of improper packing or thermal shock, thereby producing small fragments (fines) 16 that occlude the interstices between the packing particles, as shown in FIG. 1B. As a result, the flow of gas is partially blocked during adsorption and desorption, again degrading the efficiency of the sorbent tube.

SUMMARY OF THE INVENTION

Accordingly, the present teachings provide systems and methods for determining a geometric measure of a sorbent tube ("tube") based on determining a differential pressure across the tube and relating the same to a measurement for determining a differential pressure along the adsorbent material which when related to a flow rate at the vessel outlet and a viscosity of the carrier gas, provides a unit flow per unit pressure for said carrier gas in said vessel. The sensor(s) can include at least one sensor for measuring a pressure at the vessel inlet and a pressure at the vessel outlet.

In an embodiment, the invention comprises a method of performing a chromatographic analysis, including providing a carrier gas inlet for supplying carrier gas, providing a chromatographic column for receiving the carrier gas, providing a vessel having an adsorbent disposed therein for adsorbing and desorbing analytes to be measured, the vessel having an inlet and an outlet for communicating carrier gas through the vessel, communicating carrier gas from the carrier gas inlet, into the vessel through the vessel inlet, and out of the vessel through the vessel outlet, and determining the impedance of the gas communicated through the vessel.

In one embodiment, the invention comprises a chromatographic system, including a carrier gas inlet for supplying carrier gas, a chromatographic column for receiving the carrier gas, a flow path through which the carrier gas is communicated from the carrier gas inlet to the chromatographic column, a vessel disposed in the flow path, the vessel having an adsorbent disposed therein for adsorbing and desorbing analytes to be measured, wherein the vessel includes an inlet and an outlet for communicating the carrier gas through the vessel, and at least one sensor in communication with the flow path adjacent at least one of the vessel inlet and the vessel outlet for measuring at least one characteristic of the gas communicated through the vessel.

BRIEF DESCRIPTION OF THE DRAWINGS

FIG. 6A is a schematic view showing additional detail of the measurement of the gas flow through the vessels of FIG. 3;

FIG. 6B is a schematic view showing additional detail of the measurement of the gas flow through the vessels of FIG. 3;

FIG. 6C is a schematic view showing additional detail of the measurement of the gas flow through the vessels of FIG. 3;

DETAILED DESCRIPTION OF THE DRAWINGS

Figure 1A:
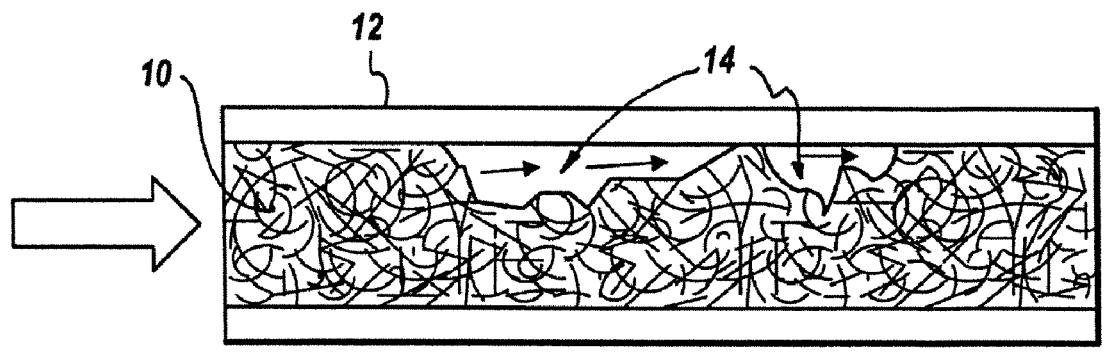
FIG. 1A is an exposed side view of a sorbent tube illustrating voids in an adsorbant.
Figure 1B:
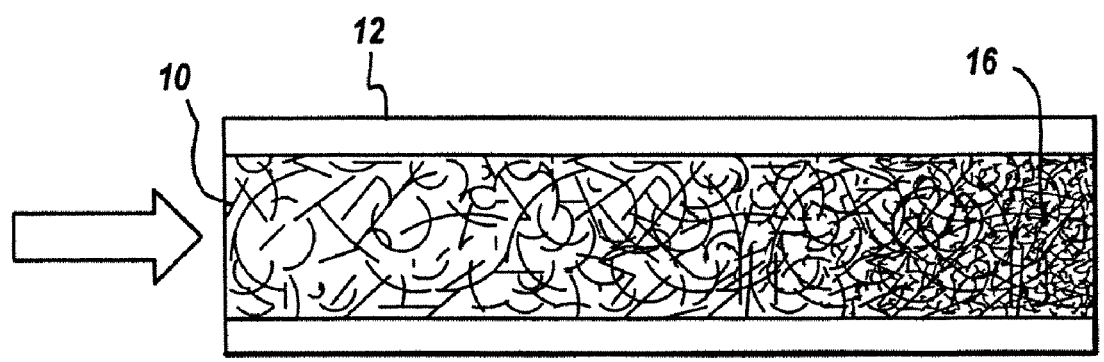
FIG. 1B is an exposed side view of a sorbent tube illustrating occlusions in interstices between packing particles of an adsorbant.
Figure 2A:
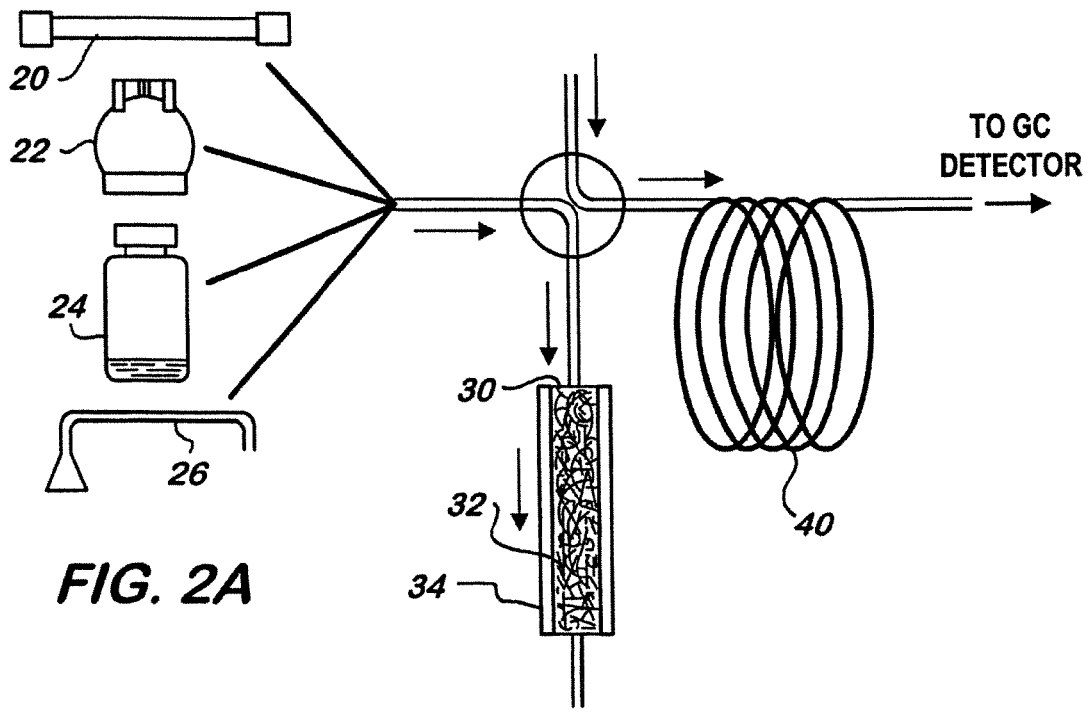
FIG. 2A is a schematic view of an example chromatographic system that may be used during a trap load stage.
Figure 2B:
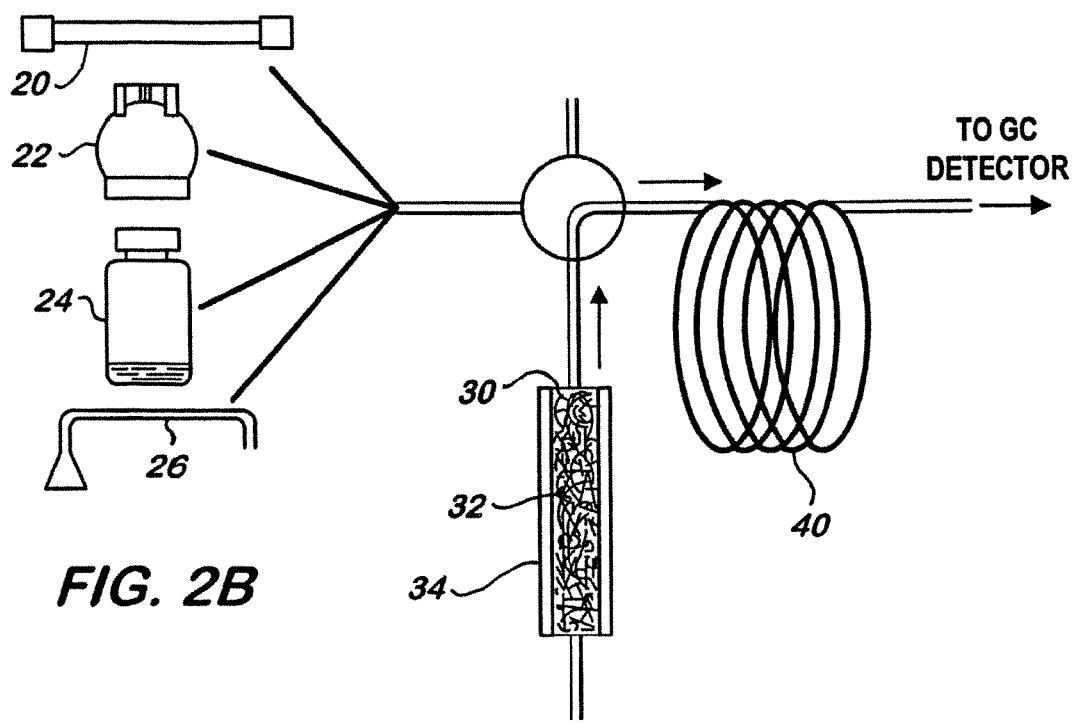
FIG. 2B is a schematic view of the chromatographic system of FIG. 2A during a trap desorb stage.

The basic components of one embodiment of a chromatographic system that verifies the integrity of a sorbent tube in accordance with the present teachings are illustrated in FIGS. 2A-B. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

The chromatographic system typically includes a sample container, such as sample tube 20, canister 22, or headspace vial 24, from which a sample containing the analytes to be measured is supplied to the system, though, in some applications, a sample of the surrounding atmosphere is pumped directly into the system via an inlet 26. The sample is usually extracted from the sample container or placed in a flow path of carrier gas, and the gas carries the sample through the system, as is further described below. As shown in FIG. 2A, the sample is typically first carried through an analyte pre-concentrator, which, in some embodiments, comprises a vessel 30, such as a tube, with an adsorbent 32 disposed therein, often referred to as an adsorbent trap. As shown in FIG. 2B, after the adsorbent 32 adsorbs the analytes and the remainder of the gas mixture passes through the vessel 30 and vents from the system, the vessel 30 is heated by a heating element 34 and the analytes are desorbed into a chromatographic column 40.

Figure 3:
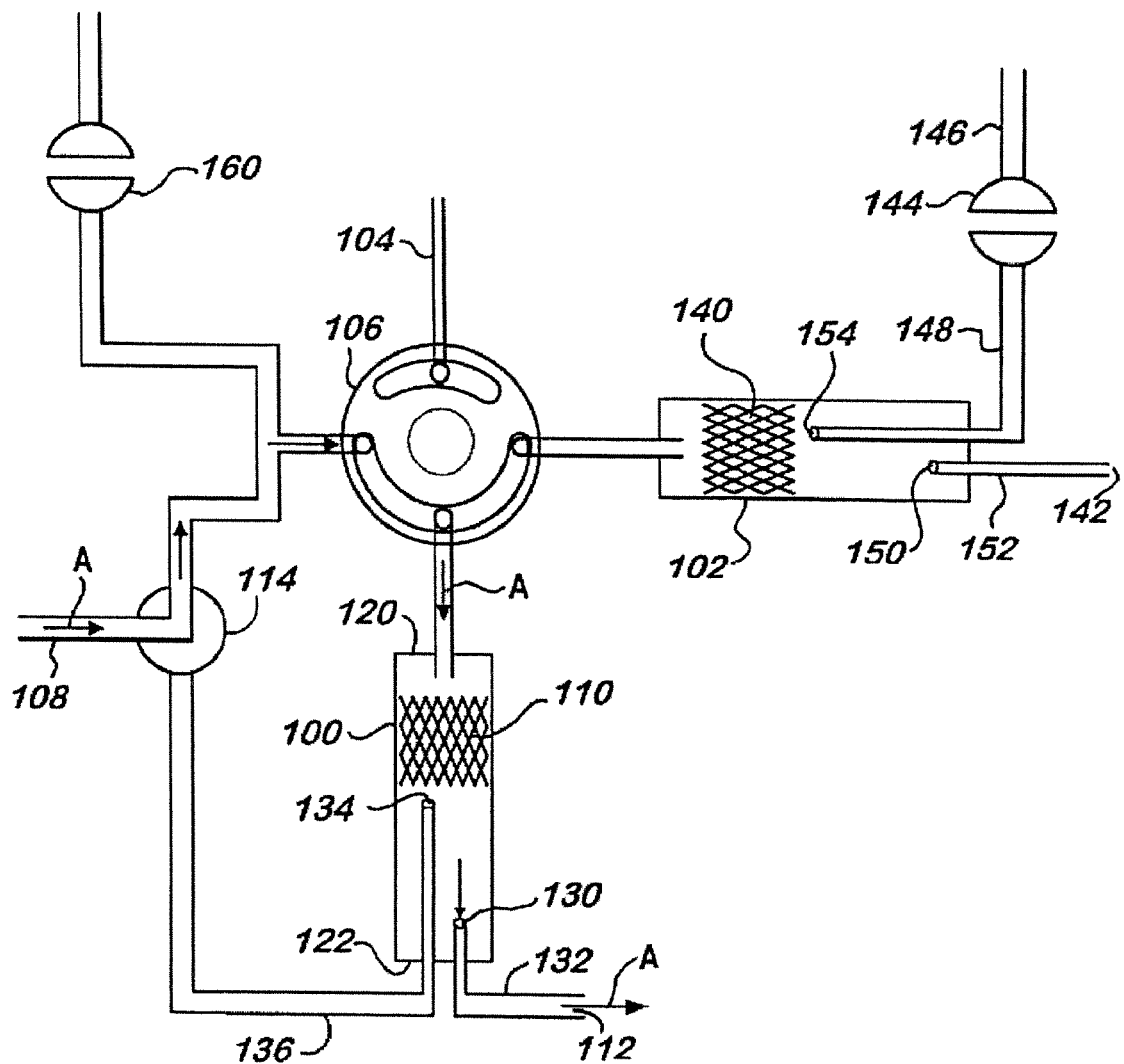
FIG. 3 is a schematic view showing additional detail of the system of FIGS. 2A-B during a sample vessel dry purge stage.

A system utilizing a thermal desorption unit for testing samples collected in sample tubes is shown in detail in FIG. 3. In these systems, a vessel, such as the sorbent tube 100, is transported to a location from which a sample is to be collected. Depending on the particular application, the sample may be collected in the vessel 100 in different ways, such as, for example, by pumping the sample into the vessel 100, or, in a particular environment to be tested, by allowing components in the air to simply migrate into the vessel 100 through natural diffusion. The vessel 100 is then transported to the thermal desorption device, where it may be placed in fluid communication with a separate adsorbent trap 102 for further concentration of the analytes prior to desorption into the chromatographic column 104.

Figure 4:
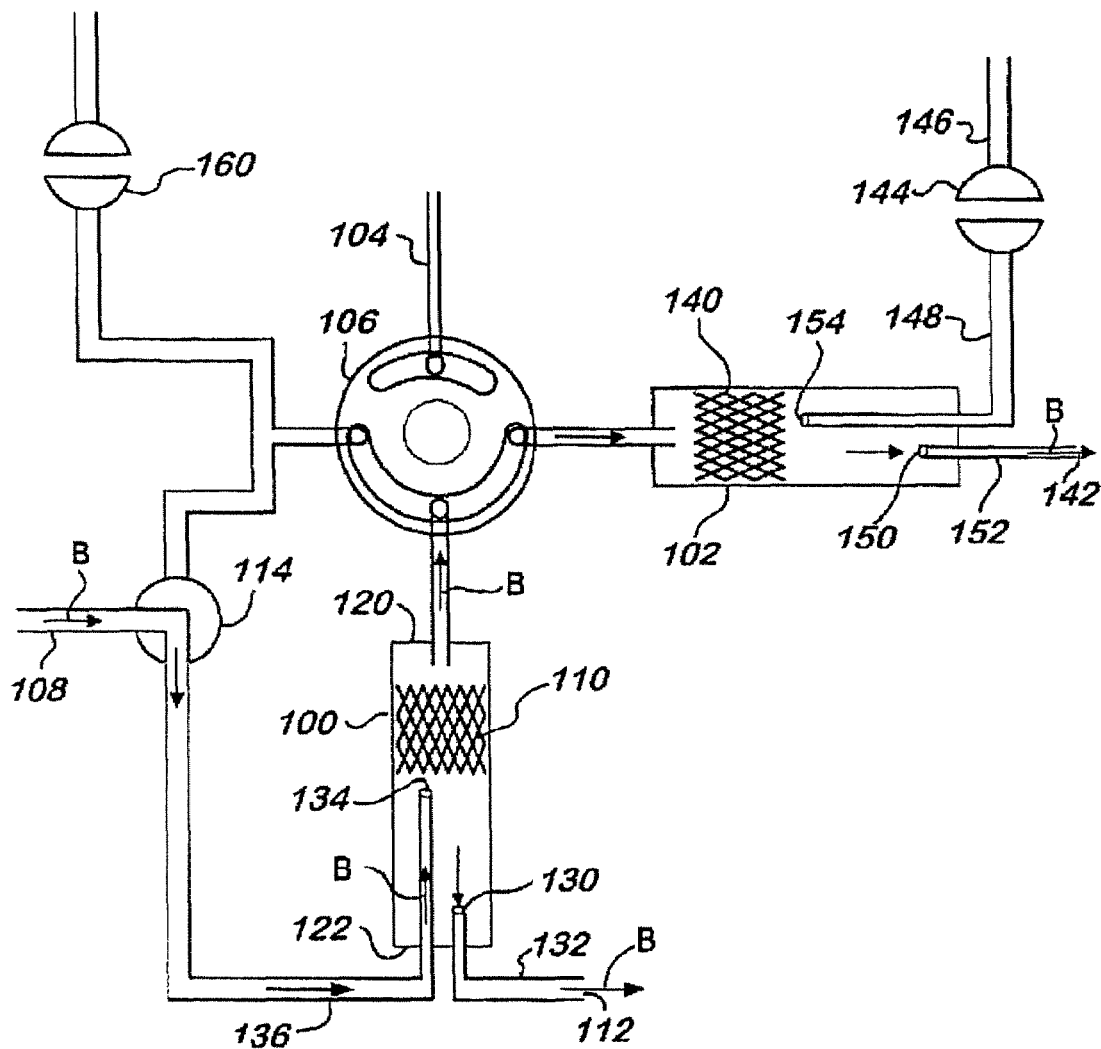
FIG. 4 is a schematic view of the system of FIG. 3 during a sample vessel desorption and trap load/purge stage.
Figure 5:
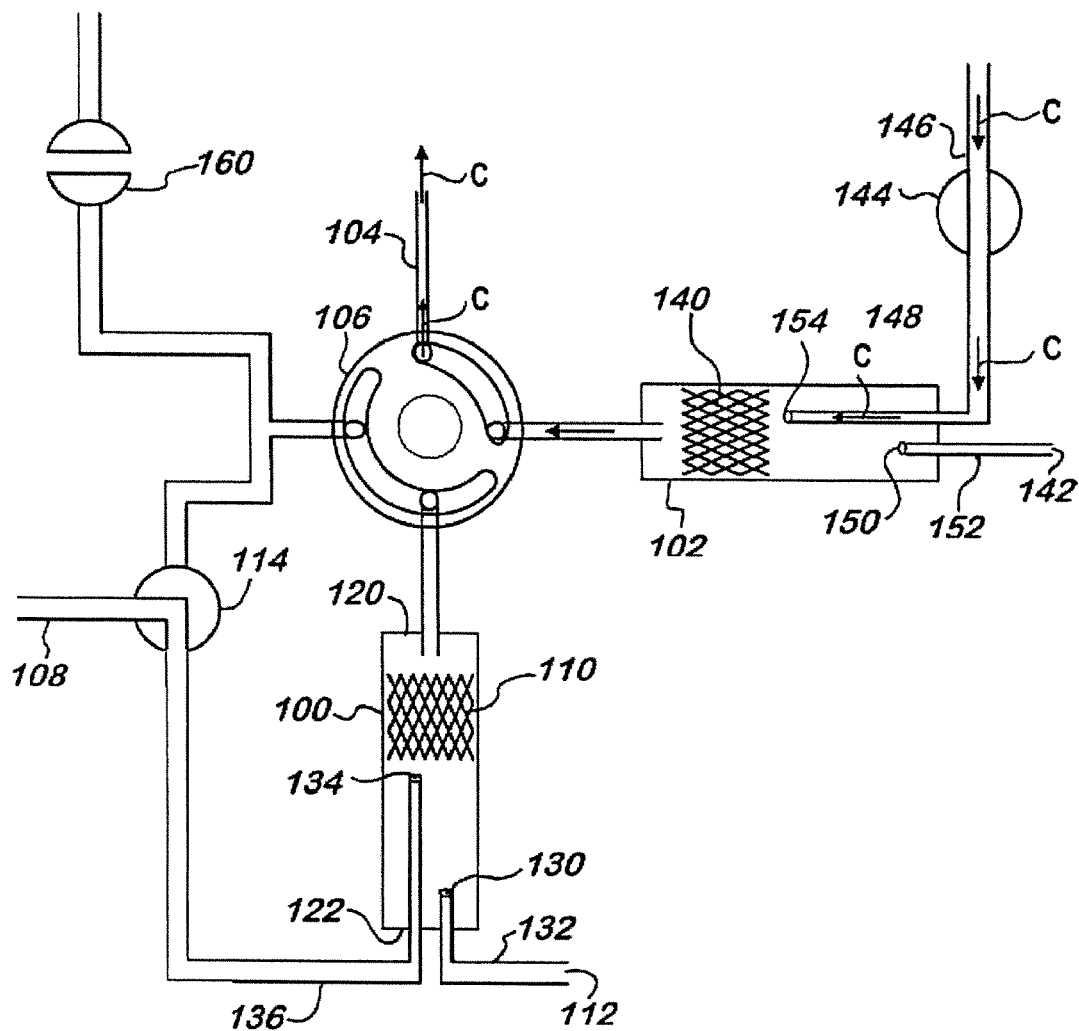
FIG. 5 is a schematic view of the system of FIG. 3 during a trap desorption stage.

The operation of this system is illustrated stepwise in FIGS. 3-5. A sample vessel dry purge step is illustrated in FIG. 3. As shown therein, a rotary valve 106 is positioned such that a carrier gas inlet 108, the sample vessel 100, and the trap 102 are in fluid communication. Carrier gas flows from the inlet 108 to the first end 120 of the sample vessel 100. The gas enters the vessel 100 through the first end 120, flows through the adsorbent 110, flows out of the vessel 100 via the inlet 130 of conduit 132, and exits through the vent 112, indicated by arrows A. In this way, moisture in the vessel 100 is purged therefrom. In certain embodiments, a valve 160 is also provided in the event a split flow is desired.

A sample vessel desorption and trap load/purge step is illustrated in FIG. 4. As shown therein, a diverter valve 114 directs carrier gas from the inlet 108 to the second end 122 of the sample vessel 100. The carrier gas flows into the vessel 100 via the outlet 134 of the conduit 136, through the adsorbent 110, out through the first end 120 of the vessel 100, and into the trap 102, indicated by arrows B. In this way, the carrier gas, sweeps up the analytes as they are desorbed from the adsorbent 110 and carries them into the trap 102. The adsorbent 140 in the trap 102 adsorbs the analytes, and the carrier gas flows out of the trap 102 via the inlet 150 of the conduit 152 and exits through the vent 142, also indicated by arrows B.

A trap desorption step is illustrated in FIG. 5. As shown therein, the rotary valve 106 is rotated and the valve 144 is opened. Carrier gas flows from the inlet 146, through the conduit 148, and into the trap 102 via the outlet 154. The gas then flows through the adsorbent 140, sweeping up the analytes as they are desorbed, and carries them out of the trap 102 and into the chromatographic column 104, indicated by arrows C.

Because the sample tube 100 and the trap 102 each comprise a vessel packed with an adsorbent, either one of them, or both, could have undesired formation of channels or fines, as previously discussed. The presence of these channels and/or fines will alter the pneumatic impedance of the trap, and therefore, the system described herein checks for alterations in this impedance in order to determine whether the results of any chromatographic analysis have been degraded as a result of the integrity of the tube and/or trap being compromised.

Figure 7:
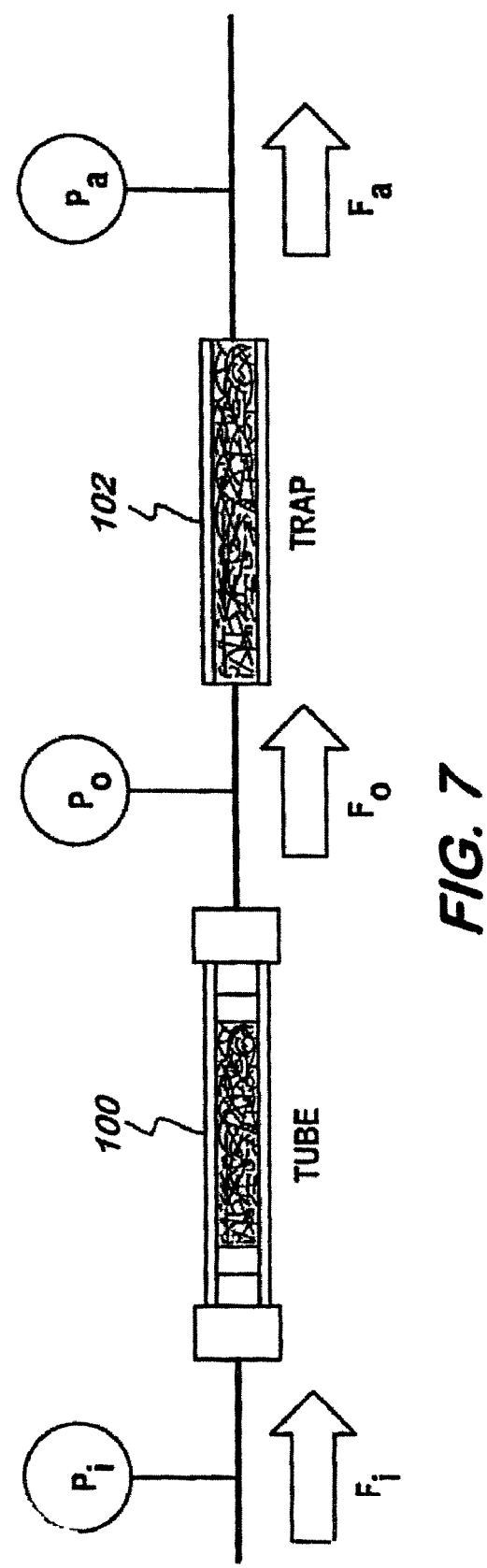

This impedance measurement can be achieved by elevating the pressures in the internal flow paths of the system, as can be seen by referencing FIG. 7 and measuring characteristics of the gas flowing through the vessel 100 and/or 102 and comparing the measured characteristics with expected values of such characteristics. Expected values of some characteristics are provided herein as examples, and it can be understood that other characteristics and/or ways of computing such expected characteristics can be varied without departing from the scope of the present teachings.

For example, in one embodiment, the sorbent tubes 100, 102 can be understood to be the geometric equivalent of a short, packed, gas chromatographic column, and therefore, the permeability of the sorbent tube can be represented according to the following equation:

$$B^o = \frac{2 \cdot \eta \cdot \varepsilon \cdot L \cdot p_o \cdot u_o}{(p_i^2 - p_o^2)} \tag{1}$$

Where:
  $B^o$ is the specific permeability coefficient
  $\eta$ is the viscosity of the gas flowing through the tube
  $\varepsilon$ is the inter-particle porosity of the adsorbent packing
  L is the length of the tube
  $p_i$ is the absolute gas pressure at the tube inlet
  $p_o$ is the absolute gas pressure at the tube outlet
  $u_o$ is the gas velocity at the tube outlet at pressure $p_o$ The inter-particle porosity of the packing $\varepsilon$ may, in turn, be represented according to the following equation:

$$\varepsilon = \frac{V_i}{V_c} \tag{2}$$

Where:
  $V_i$ is the inter-particle volume
  $V_c$ is the volume of the empty tube The gas velocity at the tube outlet $u_o$ can be represented by rearranging Equation 1 as follows:

$$u_o = \frac{B^o \cdot (p_i + p_o) \cdot (p_i - p_o)}{2 \cdot \eta \cdot \varepsilon \cdot L \cdot p_o} \tag{3}$$

Because $p_i \approx p_o$, Equation 3 may be further simplified as follows:

$$u_o = \frac{B^o \cdot (p_i - p_o)}{\eta \cdot \varepsilon \cdot L} \tag{4}$$

Accordingly, it is established that the velocity through the sorbent tube is proportional to the pressure difference across it.

The volumetric flow rate at the tube outlet can be represented according to the following equation:

$$F_o = u_o \cdot A_i \tag{5}$$

Where $A_i$ is the inter-particle area. The inter-particle-to-open-tube-area ratio should be the same as the volumetric ratio (which, according to Equation 2, is equal to the packing porosity), as shown in the following equation:

$$\frac{A_i}{A_c} = \frac{V_i}{V_c} = \varepsilon \tag{6}$$

Where $A_c$ is the cross sectional area of the empty tube. Therefore, the inter-particle area $A_i$ can be represented as follows:

$$A_i = A_c \cdot \varepsilon \tag{7}$$

Thus, the substitution of Equation 7 into Equation 5 yields the following representation of the volumetric flow rate:

$$F_o = u_o \cdot A_c \cdot \varepsilon \tag{8}$$

Because the cross-sectional area of a cylindrical tube $A_c$ is equal to $$\frac{\pi \cdot d_c^2}{4},$$

Equation 8 becomes:

$$F_o = \frac{\pi \cdot u_o \cdot d_c^2 \cdot \varepsilon}{4} \quad (9)$$

Substituting the gas velocity at the tube outlet $u_o$ of Equation 4 into Equation 9 yields the following representation of the volumetric flow rate:

$$F_o = \frac{B^\circ \cdot \pi \cdot d_c^2 \cdot (p_i - p_o)}{4 \cdot \eta \cdot L} \quad (10)$$

For a given tube at constant temperature, $B^\circ$, $d_c$, $\eta$ and L should all be constant, which can collectively be represented by the constant k, yielding the following equation:

$$F_o = \frac{k \cdot (p_i - p_o)}{\eta} \quad (11)$$

Where k is a constant and equal to $$\frac{B^\circ \cdot \pi \cdot d_c^2}{4 \cdot L}.$$

Accordingly, expressing equation 11 in terms of k allows for a characterization of the tube in terms of unit flow per unit pressure drop for a given temperature. k can thus be understood to be a geometric measure of the tube rather than the ambient conditions to which the tube is exposed. With further reference to Equation 11, once a differential pressure of the adsorbent material is obtained using, for example, one or more sensors, such differential pressure can be related to the flow rate at the output of the tube to characterize the tube based on a unit flow per unit pressure drop.

The value of $F_o$ in Equation 11 would represent the flow rate at pressure $p_o$. Normally, flow rates are expressed assuming ambient conditions (e.g. Standard Ambient Temperature and Pressure at 25° C. and 100 kPa). Accordingly, a correction may be made in accordance with the following equation:

$$F_a = F_o \cdot \frac{p_o}{p_a} \cdot \frac{T_a}{T_o} \quad (12)$$

Where:
$F_a$ is the equivalent flow rate at ambient pressure and temperature
$p_a$ is the ambient absolute pressure
$T_a$ is the ambient absolute temperature
$T_o$ is the absolute temperature at the tube outlet Accordingly, Equation 11 becomes the following equation:

$$F_a = \frac{k \cdot (p_i - p_o)}{\eta} \cdot \frac{p_o}{p_a} \cdot \frac{T_a}{T_o} \quad (13)$$

As provided herein, the constant k is a geometric measure of the tube as it is based on the geometry of the particular tube (L and $d_c$) and specific permeability of the packing therein ($B^\circ$). Therefore, constant k may be called the "permeability factor" of a sorbent tube. Once the value of k is known for a given tube, the flow rate for a given pressure drop across the tube, or the pressure drop for a given flow rate, may be calculated according to Equation 13.

Accordingly, there are several ways that an alteration in the impedance of the tubes 100, 102 can be determined, some of which are illustrated in FIGS. 6A-F. For example, in some embodiments, this determination is made by measuring the pressure drop across the tube while carrier gas flows through the tube at a known flow rate. Typical flow rates employed for this purpose fall in the range of about 20 mL/min to about 200 mL/min, and in some embodiments, more specifically around 50 mL/min, although such example flow rates are provided for illustration and not limitation.

As illustrated in FIG. 6A, in some embodiments, a flow controller 200, such as an electronic mass flow controller, is placed in the flow path of the carrier gas in order to control the flow rate of the gas, and a differential pressure transducer 202 is placed in communication with the flow path to provide pressure measurements to measure the pressure drop across the tube 102, which in some embodiments can include sensors at the inlet or outlet of the tube to derive the pressure drop by subtraction. A forward pressure regulator 230 can be used to deliver carrier gas at a known and consistent pressure to the tube. A pressure transducer 206 can be included in the circuit either upstream (as shown) or downstream of the tube to provide the absolute or gauge pressure of the gas within the tube to allow calculation of the gas flow rate at the tube exit at the applied pressure. In instances where the measurement is being made at a temperature other than ambient, a temperature sensor 233 held proximal to the tube is used to calculate the gas flow rate at the tube exit at the temperature applied there. While in certain embodiments, the flow controller 200 is placed downstream of the vessel 102, in some embodiments, as illustrated in FIG. 6B, a flow controller 204 is placed upstream of the vessel 102. As also shown therein, in some embodiments, a first transducer 206 is placed approximate the vessel inlet, and a second transducer 208 is placed approximate the vessel outlet, to provide measurements associated with the absolute or gauge pressure at the that point and the pressure difference across the vessel, although it can be understood that the positioning of such transducers 206, 208 may vary based on the transducer type, the application, and other design choices. As illustrated in FIG. 6C, in still other embodiments, only pressure transducer 206 is used, and a valve 220 is provided to vent the gas exiting the vessel outlet to the atmosphere at atmospheric pressure. A single gauge pressure transducer 206 is used to provide a measure of both the pressure inside the tube and the pressure drop across it.

Figure 6D:
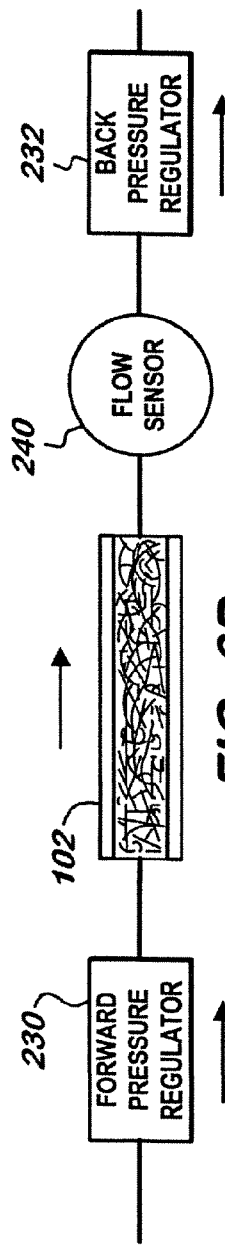
FIG. 6D is a schematic view showing additional detail of the measurement of the gas flow through the vessels of FIG. 3.
Figure 6E:
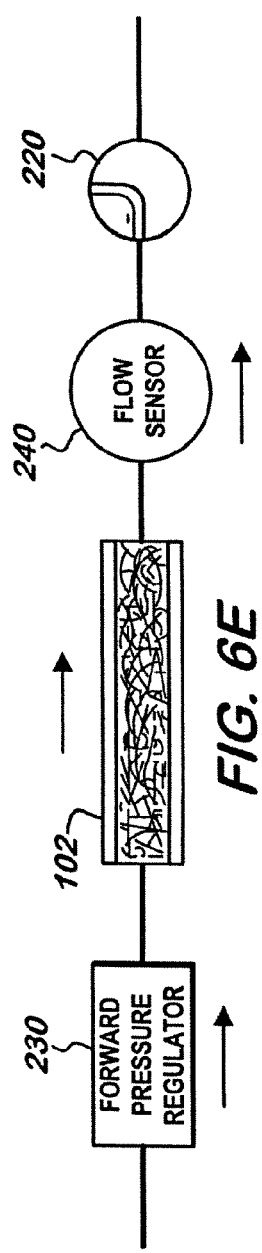
FIG. 6E is a schematic view showing additional detail of the measurement of the gas flow through the vessels of FIG. 3.
Figure 6F:
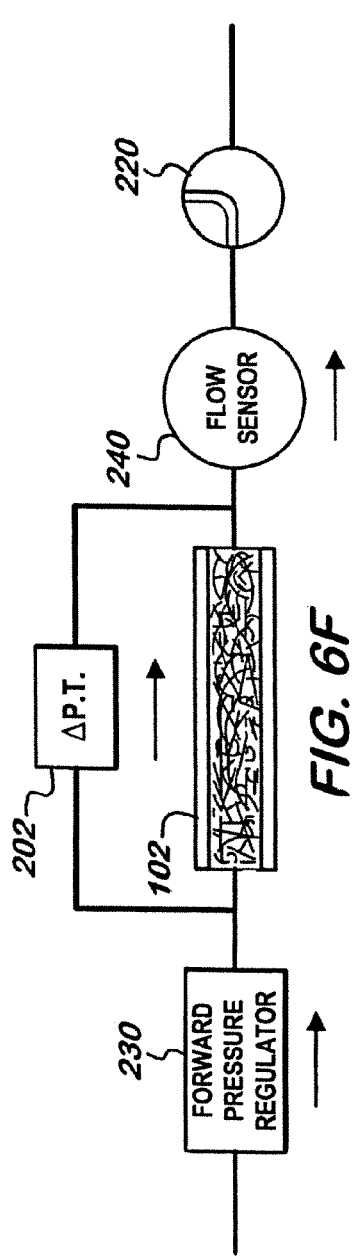
FIG. 6F is a schematic view showing additional detail of the measurement of the gas flow through the vessels of FIG. 3; and, FIG. 7 is a schematic view showing additional detail of gas flow through the vessels of FIG. 3.

In some embodiments, however, the pressure drop is known, controlled, and applied, and the flow rate is instead detected in order to measure the impedance of the vessel 102. For example, as illustrated in FIG. 6D, in some of these embodiments, a forward pressure regulator 230 is placed in the flow path between the carrier gas inlet and the vessel inlet, and a back pressure regulator 232 is placed in the flow path between the vessel outlet and the chromatographic column in order to establish the pressure drop across the vessel 102. A flow sensor 240 is then positioned at a convenient point within in the flow path in order to measure the flow rate of the gas. In embodiments, as shown in FIG. 6E, only the forward pressure regulator 230 is employed, and the valve 220, which is positioned between the vessel outlet and the chromatographic column, vents the gas to atmosphere at atmospheric pressure. As shown in FIG. 6F, in some of these embodiments that use pressure regulators to establish the pressure drop, a differential pressure transducer 202 is placed in communication with the flow path adjacent the vessel inlet and outlet in order to verify the pressure drop established by the pressure regulator 230 and the regulator 232 or valve 220.

In these ways, changes in the pneumatic impedance of sorbent tubes can be detected as part of the chromatographic analysis, both for tubes employed as adsorbent traps, where the aging effects on the integrity of the packing is of particular concern, and for sample tubes used to collect and supply the sample for analysis, where variations from tube to tube can otherwise prove problematic. In embodiments, the specific method of measurement is standardized so that meaningful results can be obtained so that the tube impedance can be tracked over the life of the tube. Further, in embodiments, the tube is kept at ambient temperature (typically in the range of about 20 to about 25 degrees Celsius) during measurement in order to reduce error.

It should be understood that the foregoing is illustrative and not limiting, and that obvious modifications may be made by those skilled in the art without departing from the spirit of the invention. For example, throughout the entirety of the present disclosure, use of the articles "a" or "an" to modify a noun can be understood to be used for convenience and to include one, or more than one of the modified noun, unless otherwise specifically stated. Further, although the illustrated examples include a sorbent "tube", it can be understood that the present teachings are not limited to a vessel having a particular cross section, and the methods and systems are applicable to different size and shaped vessels having an adsorbent material contained and/or disposed therein. Accordingly, reference should be made primarily to the accompanying claims, rather than the foregoing specification, to determine the scope of the invention.

What is claimed is:

1. A chromatographic method, comprising:
    providing a vessel in a carrier gas flow path to a chromatographic column, the vessel comprising:
        a gas inlet,
        a gas outlet, and,
        an adsorbent disposed in the vessel,
    measuring a differential pressure along the length of the adsorbent,
    determining a flow rate at the outlet, and,
    determining a unit flow per unit pressure based on a ratio of the flow rate and the differential pressure.

2. The method of claim 1, further comprising adjusting the unit flow per unit pressure based on a viscosity of the gas.

3. The method of claim 1, further comprising at least one of:
    determining a flow rate at ambient pressure using a factor based on a ratio of a gas pressure at the output and ambient pressure, and,
    determining a flow rate at ambient temperature using a factor based on a ratio of a temperature at the output and ambient temperature.

4. The method of claim 1, further comprising heating the vessel to desorb analytes from the adsorbent.

5. The method of claim 1, wherein the vessel comprises an adsorbent trap.

6. The method claims 1, wherein the vessel comprises a sample tube.

7. The method of claim 6, further comprising:
    providing a second vessel in the carrier gas flow path to the chromatographic column, the second vessel comprising:
        a gas inlet,
        a gas outlet, and,
        an adsorbent disposed in the second vessel,
    measuring a differential pressure along the length of the adsorbent disposed in the second vessel,
    determining a flow rate at the outlet of the second vessel, and,
    determining a second unit flow per unit pressure based on a ratio of the flow rate at the outlet of the second vessel and the differential pressure along the length of the adsorbent disposed in the second vessel.

8. A chromatographic method, comprising:
    providing a vessel in a carrier gas flow path to a chromatographic column, the vessel comprising:
        a gas inlet,
        a gas outlet, and,
        an adsorbent disposed in the vessel,
    measuring a differential pressure along the length of the adsorbent, and
    relating the differential pressure to a flow rate at the outlet to determine a unit flow per unit pressure based on a ratio of the flow rate and the differential pressure.

9. The method of claim 8, further comprising adjusting the unit flow per unit pressure based on a viscosity of the gas.

10. The method of claim 8, further comprising establishing the flow rate at the outlet by controlling the flow of the gas.

11. The method of claim 8, wherein the vessel comprises an adsorbent trap.

12. The method claims 8, wherein the vessel comprises a sample tube.

13. The method of claim 12, further comprising:
    providing a second vessel in the carrier gas flow path to the chromatographic column, the second vessel comprising:
        a gas inlet,
        a gas outlet, and,
        an adsorbent disposed in the second vessel,
    measuring a differential pressure along the length of the adsorbent disposed in the second vessel, and,
    relating the differential pressure along the length of the adsorbent disposed in the second vessel to a flow rate at the outlet of the second vessel to determine a second unit flow per unit pressure based on a ratio of the flow rate at the outlet of the second vessel and the differential pressure along the length of the adsorbent disposed in the second vessel.

* * * * *